United States Patent
Buddery et al.

(10) Patent No.: US 9,114,002 B2
(45) Date of Patent: Aug. 25, 2015

(54) ENDOVASCULAR GRAFT WITH AN EXPANDED LUMEN AT A BIFURCATION

(71) Applicant: Cook Medical Technologies LLC, Bloomington, IN (US)

(72) Inventors: Alexander Buddery, Upper Mount Gravatt (AU); Chantelle King, Kelvin Grove (AU); Emma Sauer, Greenbank (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/305,132

(22) Filed: Jun. 16, 2014

(65) Prior Publication Data

US 2014/0371838 A1 Dec. 18, 2014

(30) Foreign Application Priority Data

Jun. 18, 2013 (AU) ................................. 2013206465

(51) Int. Cl.
*A61F 2/07* (2013.01)
*A61F 2/954* (2013.01)
*A61F 2/06* (2013.01)

(52) U.S. Cl.
CPC . *A61F 2/07* (2013.01); *A61F 2/954* (2013.01); *A61F 2002/061* (2013.01); *A61F 2002/065* (2013.01); *A61F 2002/075* (2013.01); *A61F 2250/0039* (2013.01)

(58) Field of Classification Search
None
See application file for complete search history.

(56) References Cited

U.S. PATENT DOCUMENTS

| 6,129,756 | A | 10/2000 | Kugler et al. |
| 6,361,637 | B2 * | 3/2002 | Martin et al. ................. 156/187 |
| 8,043,354 | B2 * | 10/2011 | Greenberg et al. .......... 623/1.12 |
| 8,709,064 | B2 * | 4/2014 | Rasmussen et al. ......... 623/1.13 |
| 2004/0098084 | A1 * | 5/2004 | Hartley et al. ............... 623/1.11 |
| 2004/0193254 | A1 * | 9/2004 | Greenberg et al. .......... 623/1.35 |
| 2006/0095118 | A1 | 5/2006 | Hartley |
| 2007/0043425 | A1 | 2/2007 | Hartley et al. |
| 2007/0250154 | A1 | 10/2007 | Greenberg et al. |

FOREIGN PATENT DOCUMENTS

| AU | 2012258394 | 3/2013 |
| EP | 14162447 | 10/2014 |
| WO | 2004019823 A1 | 3/2004 |
| WO | 2004064686 A1 | 8/2004 |
| WO | 2007124053 A1 | 11/2007 |
| WO | 2008021556 A1 | 2/2008 |

* cited by examiner

*Primary Examiner* — Tuan V Nguyen
(74) *Attorney, Agent, or Firm* — Richard J. Godlewski

(57) ABSTRACT

A stent graft for placement in a lumen of a patient is disclosed. The stent graft comprises a main body including a main lumen and having a distal end terminating in a bifurcation. It also comprises first and second legs extending from the bifurcation, the first and second legs having respective first and second leg lumens and the first and second leg lumens being in fluid communication with the main lumen; and a side arm extending from the first leg, the side arm having a side arm lumen. The side arm lumen is in fluid communication with the first leg lumen at a position adjacent to the bifurcation. A combined lumen is formed. The combined lumen is between the main lumen and a distal portion of the first leg lumen and is bounded laterally by a portion of the side arm located adjacent to the bifurcation.

18 Claims, 17 Drawing Sheets

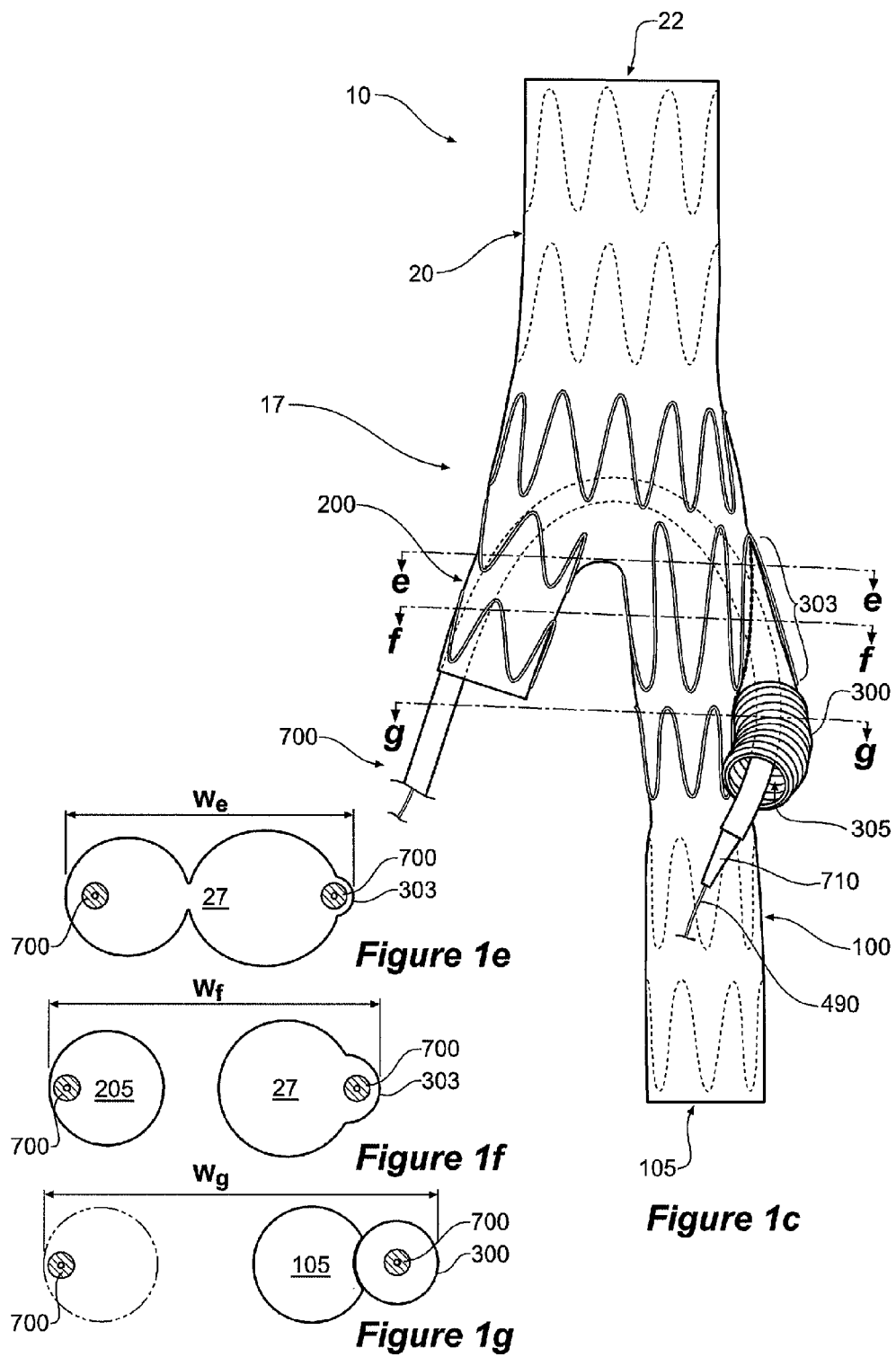

ENDOVASCULAR GRAFT WITH AN EXPANDED LUMEN AT A BIFURCATION

FIELD OF INVENTION

This invention relates to medical devices and more particularly to devices which can be deployed by endovascular means into the vasculature of a patient.

BACKGROUND OF THE INVENTION

There exist endovascular stent grafts which can be deployed into the vasculature in the region of the aortic bifurcation so as to treat aortoiliac aneurysms. These stent grafts can include an anastomosis in the region of the iliac bifurcation. Such stent grafts require the insertion of a covered stent to bridge the gap between the endovascular graft and the internal iliac artery. A preferred method of introducing the covered stent is to insert the stent through the iliac/femoral artery on the contralateral side and guide the stent up and over to the ipsilateral side where it is deployed (the "up and over" approach). With some stent grafts, a fenestration or valve is provided in the wall of the stent graft to allow temporary access for a catheter to allow deployment of the covered stent through the iliac/femoral artery. Such fenestrations or valves should be self-closing which complicates the stent graft and provides a potential leakage area.

The "up and over" approach from the contralateral side helps to maximize the diameter of the curve available for the covered stent to come around and face caudally so that it can be deployed. Maximising this curve reduces the force required to insert the sheath and catheter constraining the covered stent and also prevents kinking and facilitates easier access.

In patients with shorter common iliac arteries, the "up and over" approach becomes more challenging as the endovascular graft typically has to be inserted further above the aortic bifurcation which reduces the diameter which the sheath has to turn. Furthermore, stent grafts having fenestrations or valves are difficult to design and manufacture for patients with short common iliacs because of the lack of room on the stent graft in the region of the common iliac.

It is an object of the present invention to provide an improved stent graft that ameliorates the aforementioned problem(s) or at least offers a useful choice.

Throughout this specification, when discussing the application of this invention to the aorta or other blood vessels, the term "distal" with respect to a prosthesis is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

SUMMARY OF THE INVENTION

According to a first aspect of the invention there is provided a stent graft for placement in a lumen of a patient, the stent graft comprising a biocompatible graft material and a plurality of stents, the stent graft comprising:
a. a main body comprising a main lumen and having a proximal end and a distal end terminating in a bifurcation;
first and second legs extending from the bifurcation, the first and second legs having respective first and second leg lumens and the first and second leg lumens being in fluid communication with the main lumen;
a side arm extending from the first leg, the side arm having a side arm lumen, the side arm lumen in fluid communication with the first leg lumen at a position adjacent to the bifurcation; and
a combined lumen, the combined lumen between the main lumen and a distal portion of the first leg lumen, the combined lumen bounded laterally by a portion of the side arm located adjacent to the bifurcation.

According to a first aspect of the invention there is provided a stent graft for placement in a lumen of a patient, the stent graft comprising a biocompatible graft material and a plurality of stents, the stent graft comprising:
a main body comprising a main lumen and having a proximal end and a distal end terminating in a bifurcation;
first and second legs extending from the bifurcation, the first and second legs having respective first and second leg lumens and the first and second leg lumens being in fluid communication with the main lumen;
a side arm extending from the first leg, the side arm having a side arm lumen, the side arm lumen in fluid communication with the first leg lumen at a position laterally adjacent to the bifurcation; and
a combined lumen, the combined lumen between the main lumen and a distal portion of the first leg lumen, the combined lumen bounded laterally by a portion of the side arm located longitudinally at the point where the bifurcation begin from the proximal to the distal direction.

In one form, the main lumen comprises a divergent portion adjacent to the bifurcation, the divergent portion diverging distally.

In one form, the combined lumen at the bifurcation diverges distally.

In one form, the first leg comprises a long leg and the second leg comprises a short leg, the long leg longer than the short leg.

In one form, the stent graft comprises a plurality of longitudinally spaced apart self-expanding stents fastened thereto.

In one form, at least some of the plurality of self-expanding stents comprise zig-zag stents, each zig-zag stent comprising a plurality of struts and bends, the bends being between adjacent struts.

In one form, the stent graft comprises a body temporary diameter reduction constraint arrangement, the body constraint arrangement comprising:
a. a body release wire; and
b. a plurality of loops of thread, each loop engaged with the body release wire and engaged around a proximal portion of the main body circumferentially spaced a selected distance away from the body release wire, and drawn tight and tied to itself to reduce the proximal portion of the main body.

In one form, the stent graft comprises a leg temporary diameter reduction constraint arrangement, the leg constraint arrangement comprising:
a. a leg release wire; and
b. a plurality of loops of thread, each loop engaged with the leg release wire and engaged around a distal portion of the second leg at a location circumferentially spaced a selected distance away from the leg release wire, and drawn tight and tied to itself to reduce the distal portion of the second leg.

In one form, the leg release wire is slidably attached to the biocompatible graft material at two spaced-apart positions in, or adjacent to, the divergent portion, a. whereby the two spaced-apart positions are sufficiently spaced so as to allow the leg release wire to be retracted without excessive force.

In one form, the leg release wire curves over the bifurcation and exits out through the second leg.

In one form, the zig-zag stent is super elastic.

In one form, the side arm extends part helically around the first leg.

In one form, the side arm comprises a self-expanding helical coil stent.

In one form, the proximal end of the main body comprises an internal self-expanding sealing stent and an outer sealing surface.

In one form, the distal end of the first leg comprises an internal self-expanding stent and an external sealing surface.

According to a second aspect of the invention, there is provided an assembly comprising:

a. a delivery device;
b. the stent graft according to the first aspect of the invention loaded onto the delivery device; and
c. an indwelling catheter passing in through the side arm lumen of the side arm and out through the proximal end of the main body.

In one form, the assembly further comprises a nose cone dilator, the nose cone dilator comprising a groove, the groove receiving a tip on an end of the indwelling catheter.

In one form, the tip is curved to facilitate cannulation of the second leg.

A detailed description of one or more embodiments of the invention is provided below, along with accompanying figures that illustrate, by way of example, the principles of the invention. While the invention is described in connection with such embodiments, it should be understood that the invention is not limited to any embodiment. On the contrary, the scope of the invention is limited only by the appended claims and the invention encompasses numerous alternatives, modifications and equivalents. For the purpose of example, numerous specific details are set forth in the following description in order to provide a thorough understanding of the present invention.

The present invention may be practiced according to the claims without some or all of these specific details. For the purpose of clarity, technical material that is known in the technical fields related to the invention has not been described in detail so that the present invention is not unnecessarily obscured.

BRIEF DESCRIPTION OF THE DRAWINGS

To assist with understanding of the invention, reference will now be made to the accompanying drawings which show preferred embodiments of the invention.

In the drawings:

FIG. 1c shows the stent graft of FIGS. 1a and 1b being cannulated.

FIG. 1e shows a cross section of the stent graft of FIG. 1c through section lines e-e.

FIG. 1f shows a cross section of the stent graft of FIG. 1c through section lines f-f.

FIG. 1g shows a cross section of the stent graft of FIG. 1c through section lines g-g.

DESCRIPTION OF THE INVENTION

Figure 1A:
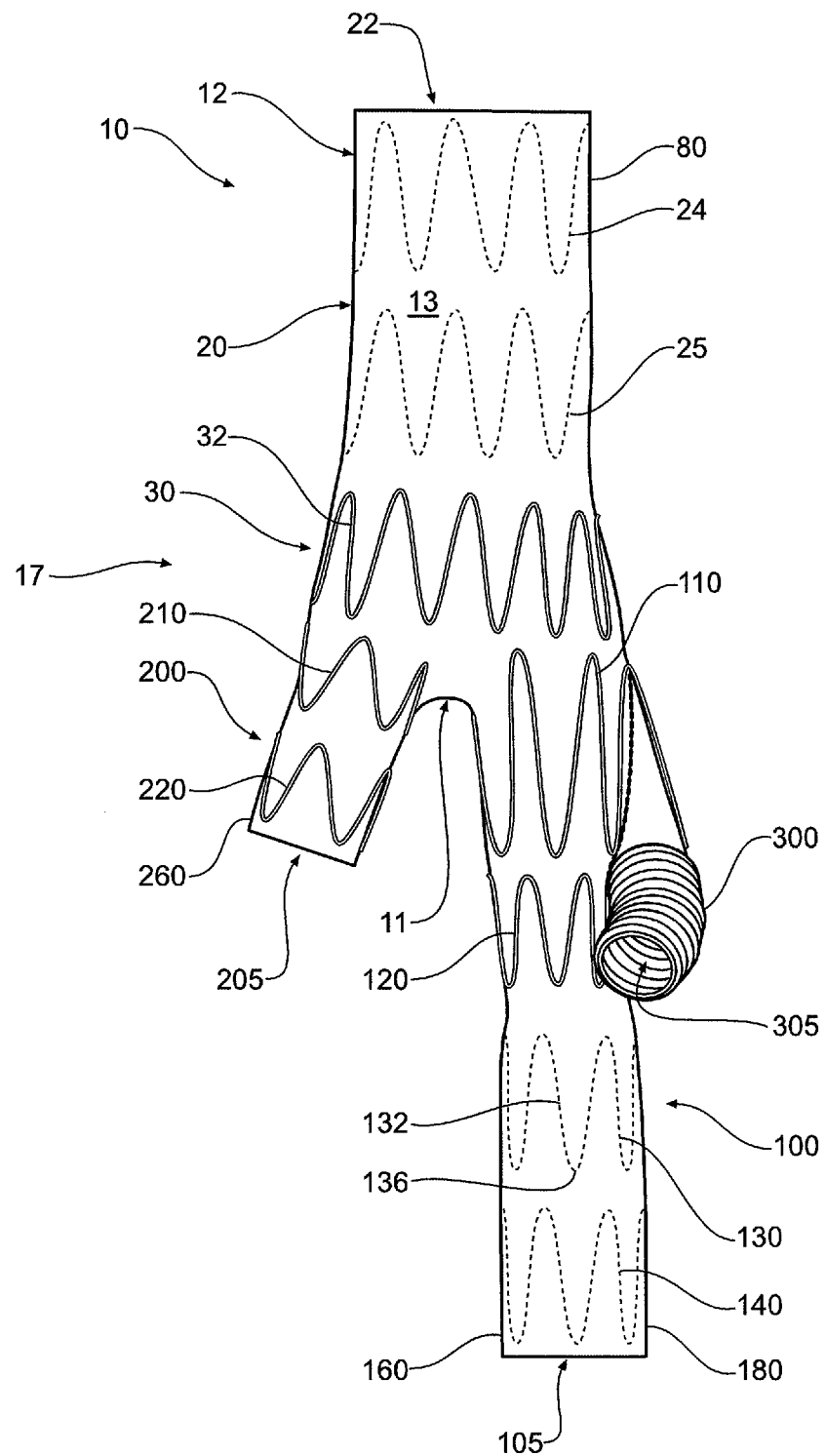
FIG. 1a shows a stent graft according to the invention.

Referring to FIG. 1a, a stent graft 10 for placement in a lumen of a patient is shown. The stent graft 10 comprises a biocompatible graft material 13 and a plurality of stents 24, 25, 32, 210, 220, 110, 120 130 140. The stents are self-expanding.

The stent graft has a main body 20 comprising a main lumen 22, a bifurcation 17 in the main body 20 and first and second legs 100, 200 fastened to and extending from the bifurcation 17.

The first and second legs 100, 200 have respective first and second leg lumens 105, 205 and the first and second leg lumens 105, 205 being in fluid communication with the main lumen 22.

A side arm 300 is fastened to the first leg 100. The side arm 300 has a side arm lumen 305 and the side arm lumen 305 is in fluid communication with the first leg lumen 105 at the bifurcation 17 thereby providing a combined and expanded lumen at the bifurcation. The expanded lumen diverges distally.

The tubular side arm 300 extends part helically around the longer leg 100 and comprises a self-expanding helical coil stent.

Figure 4A:
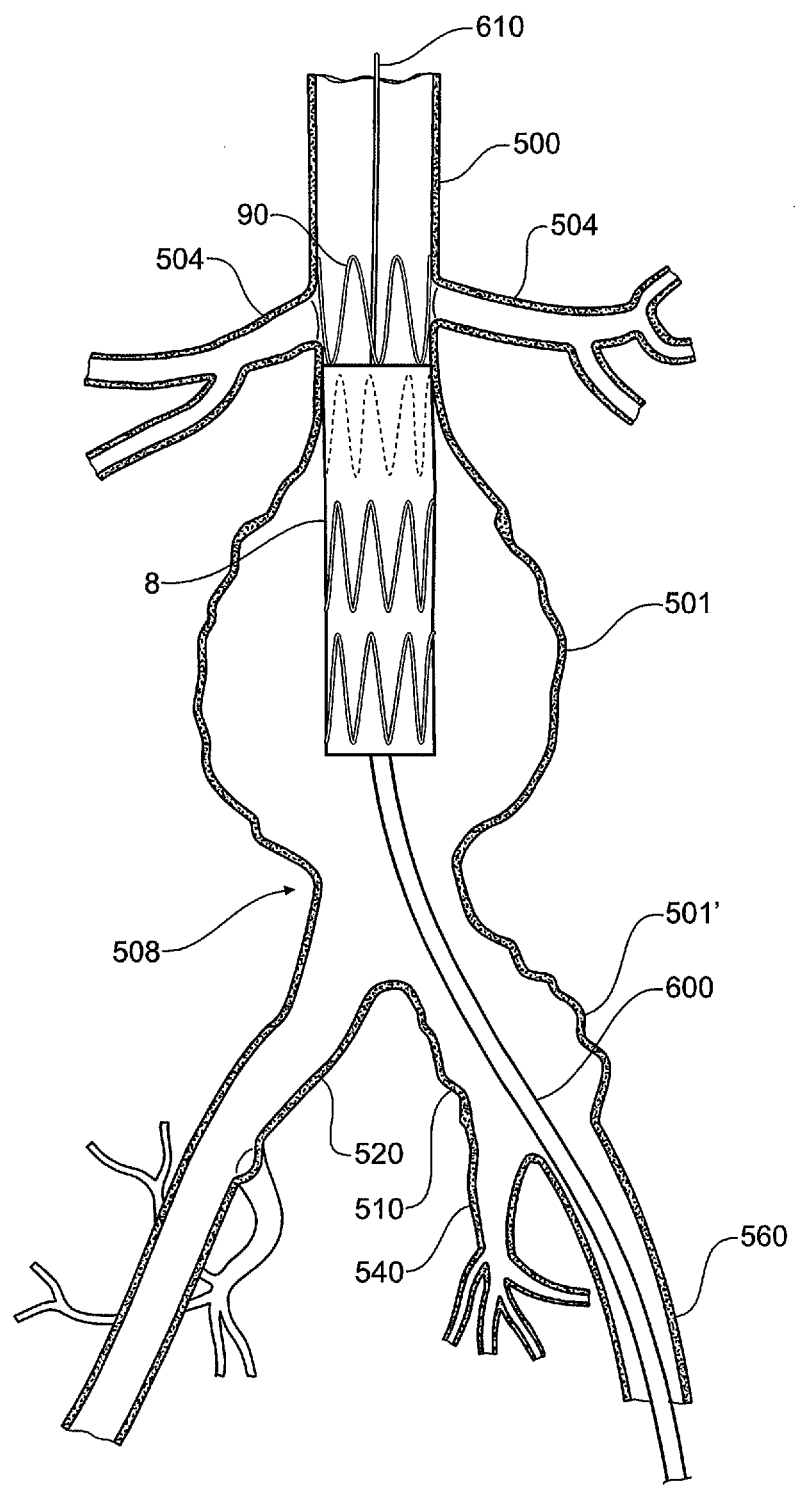
FIGS. 4a to 4j show the various stages of deployment of a stent graft according to the invention into the vascular system of a patient.
Figure 4B:
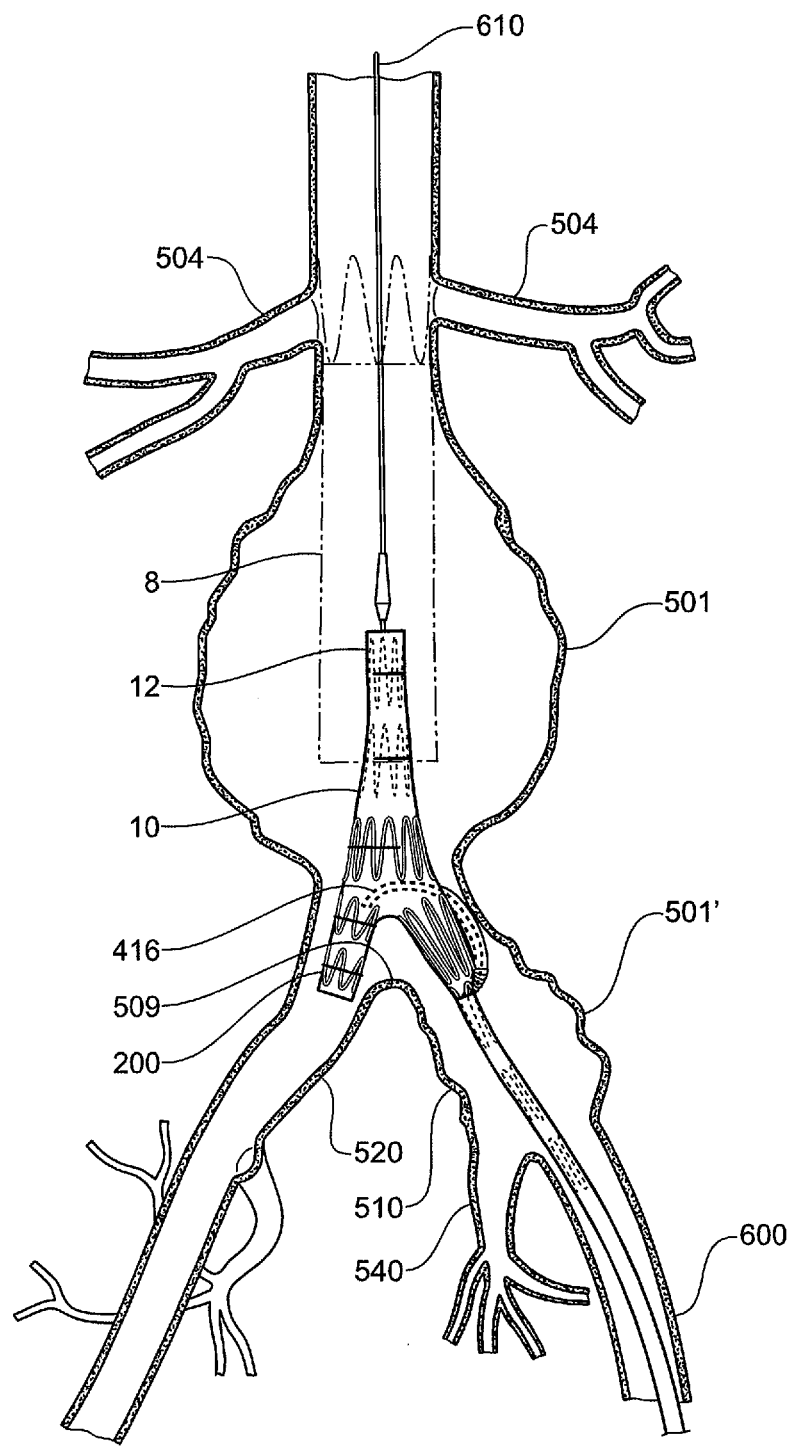
Figure 4C:
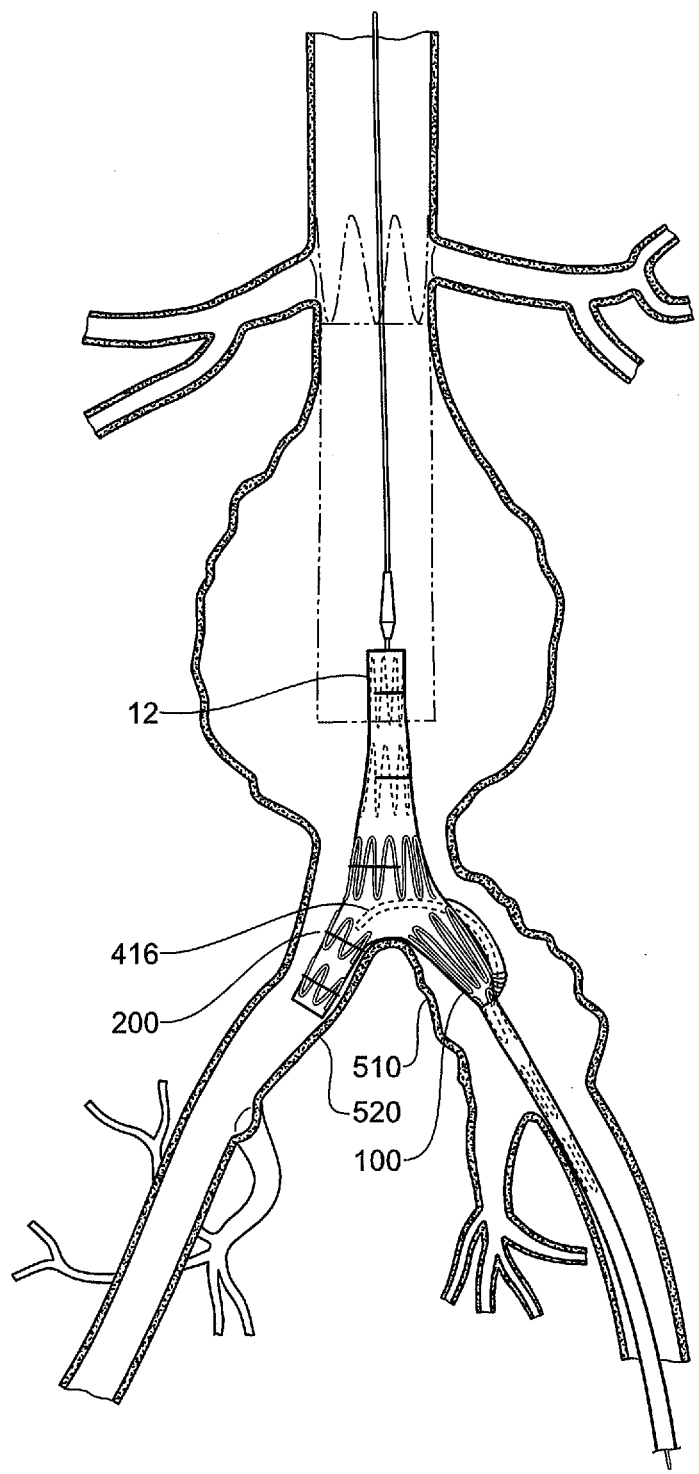
Figure 4D:
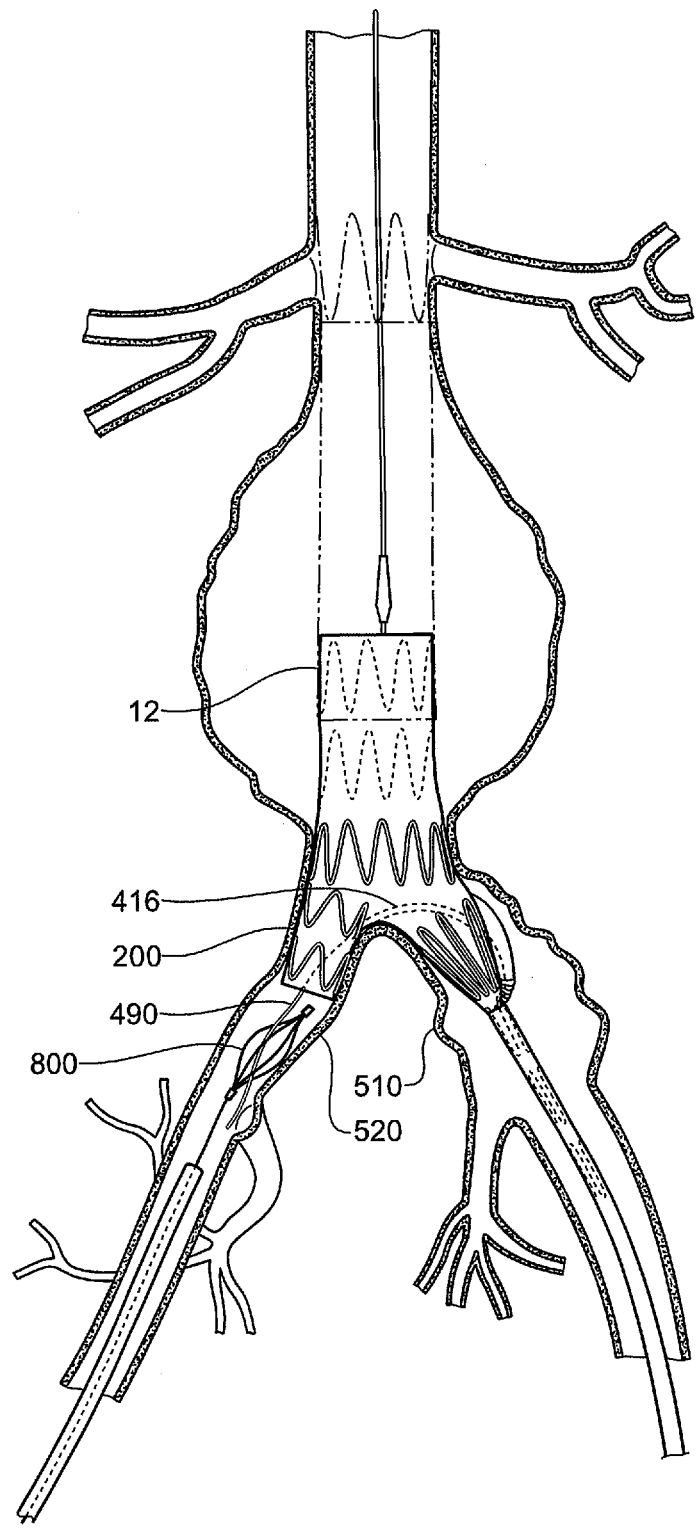
Figure 4E:
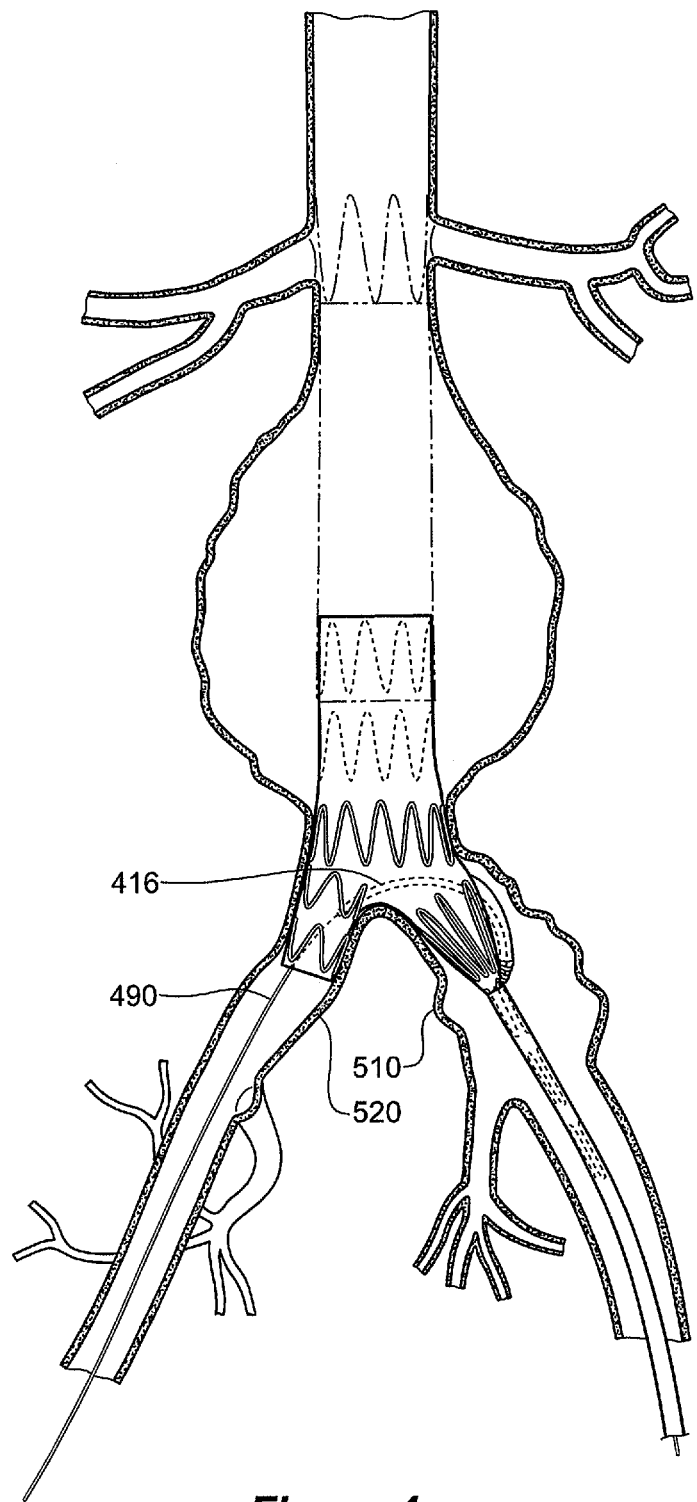
Figure 4F:
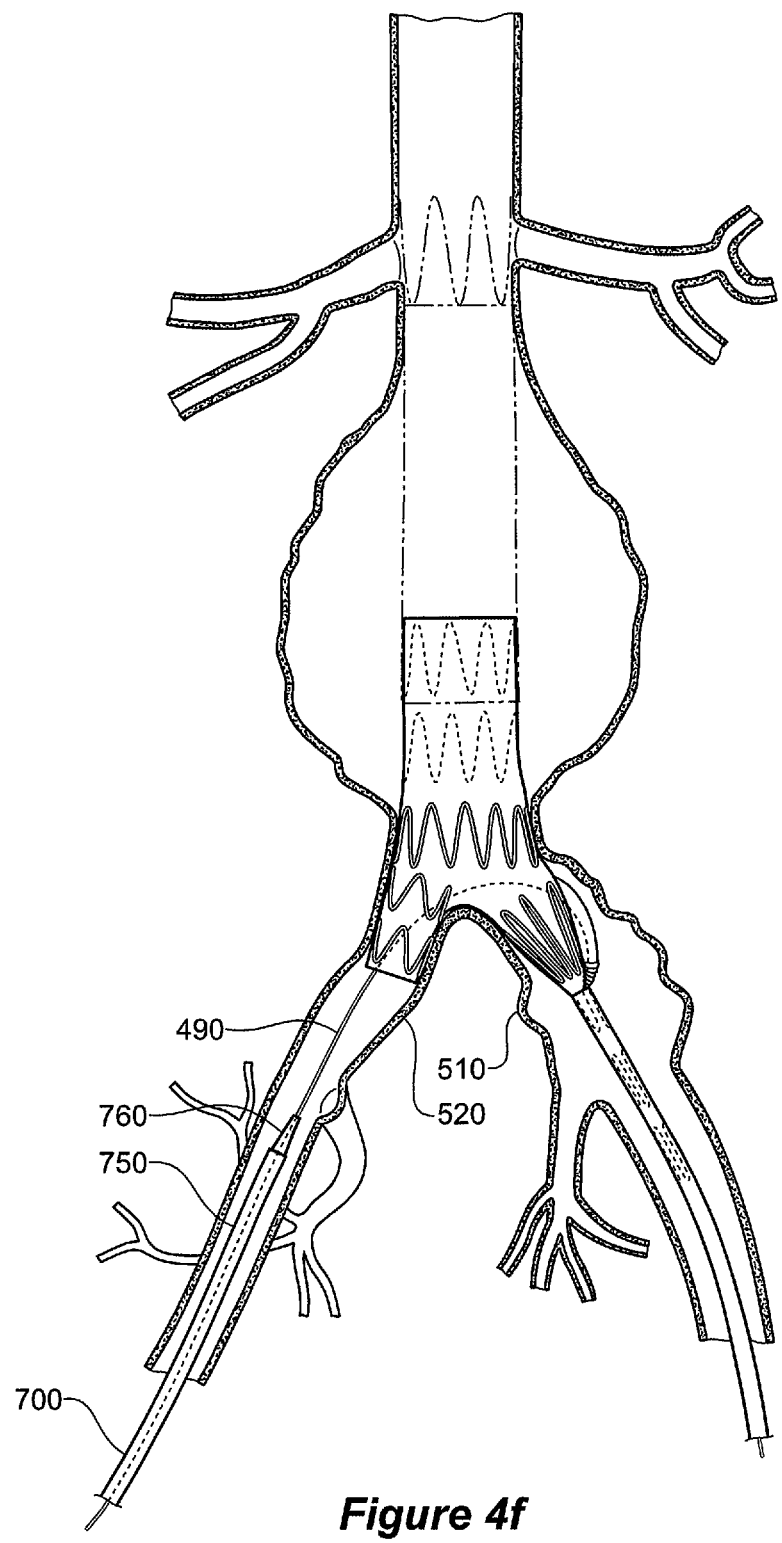
Figure 4G:
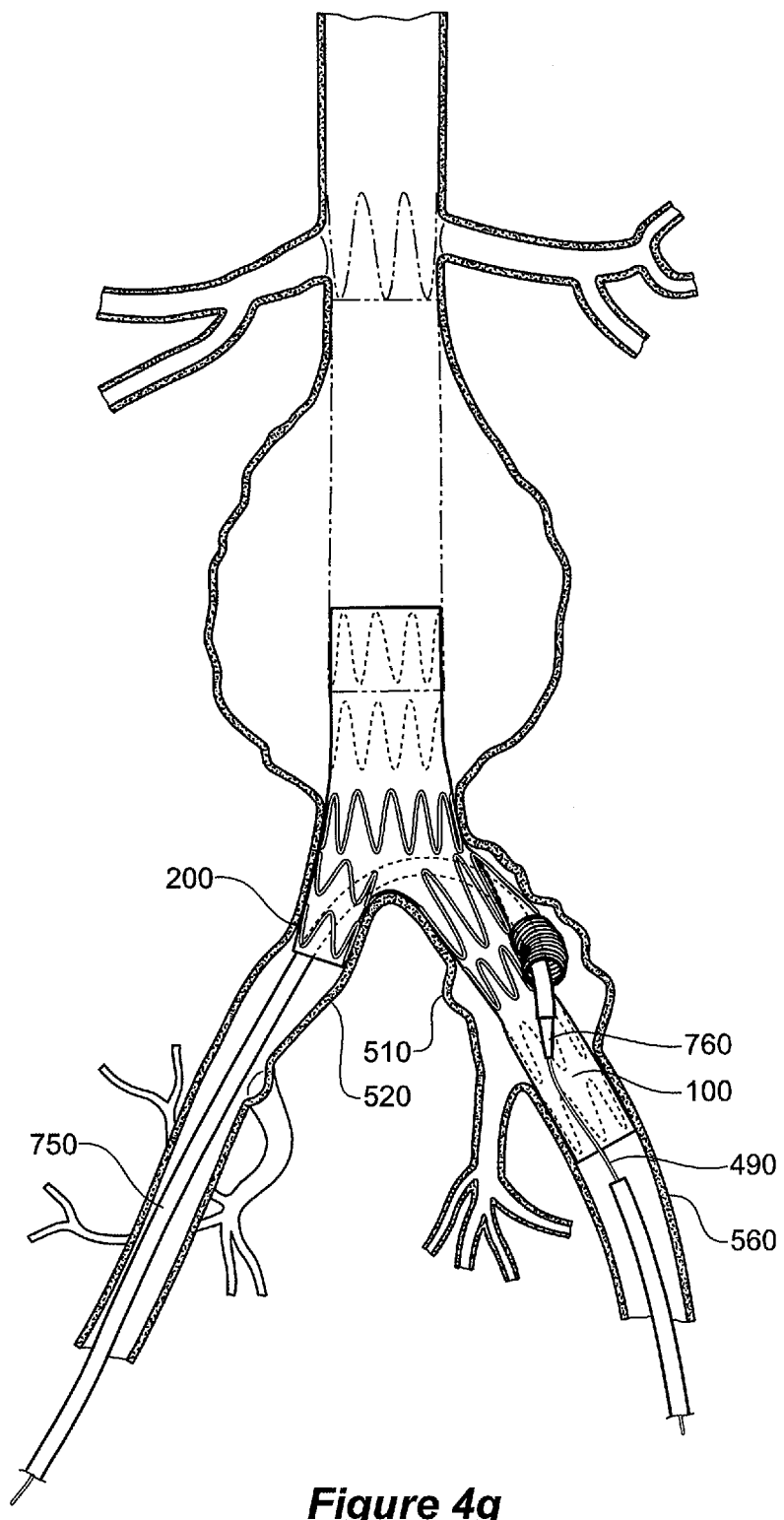
Figure 4H:
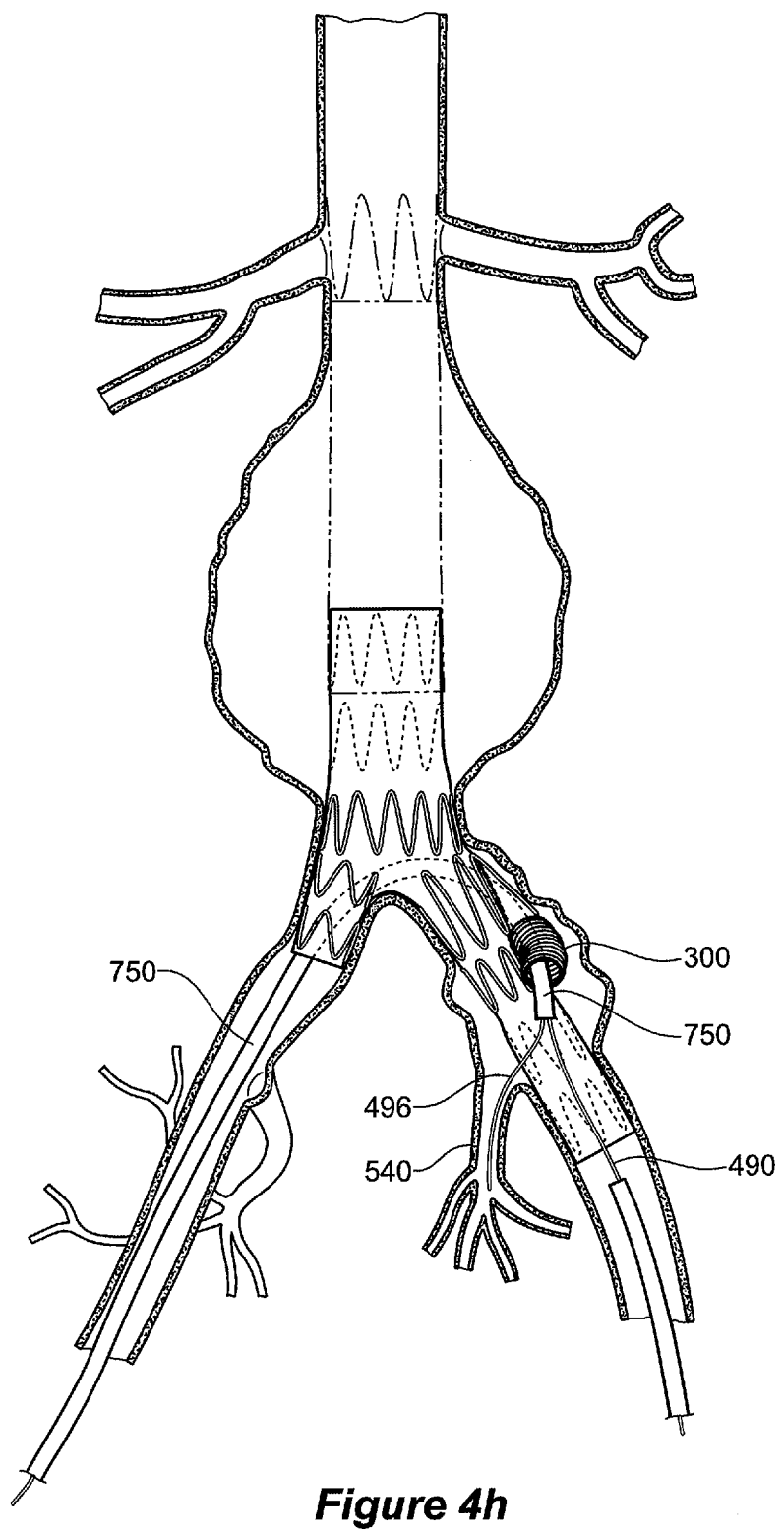
Figure 4I:
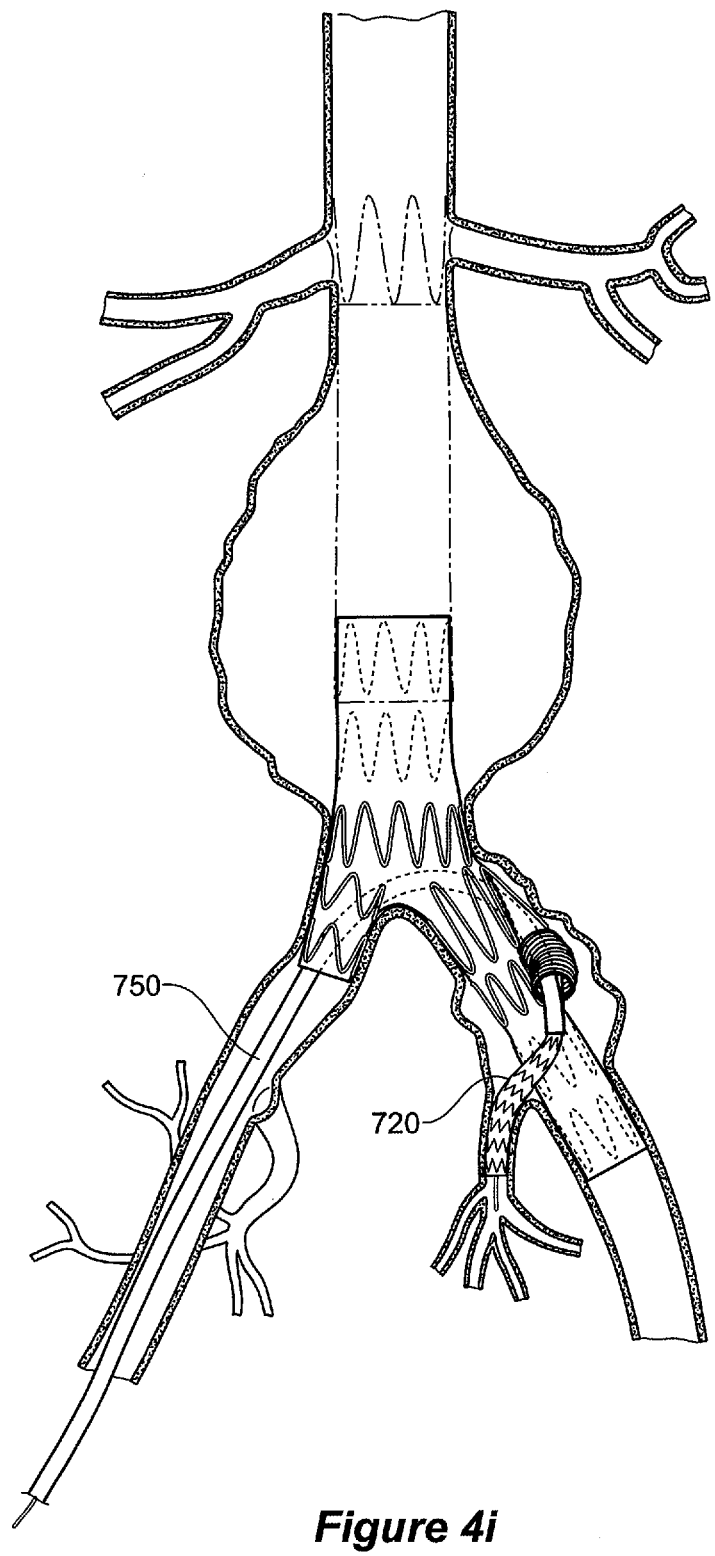
Figure 4J:
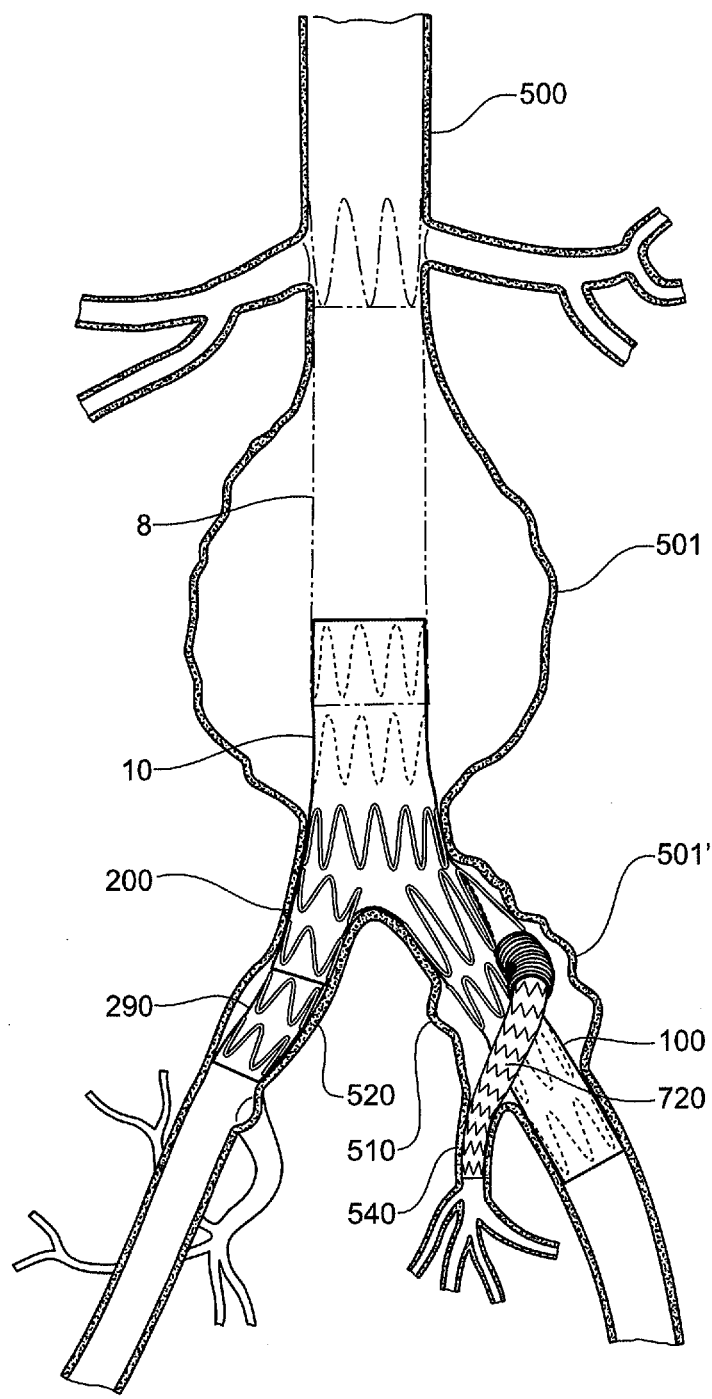

As shown in FIG. 4j, the stent graft 10 can be deployed into the vasculature of a patient with the main body 20 being in an aneurysmal portion 501 the descending aorta 500 of a patient with the first leg 100 extending down an ipsilateral common iliac artery 510, the second leg being directed towards a contralateral common iliac artery 520 and the side arm on the first leg directed to an internal iliac artery 540.

Figure 1B:
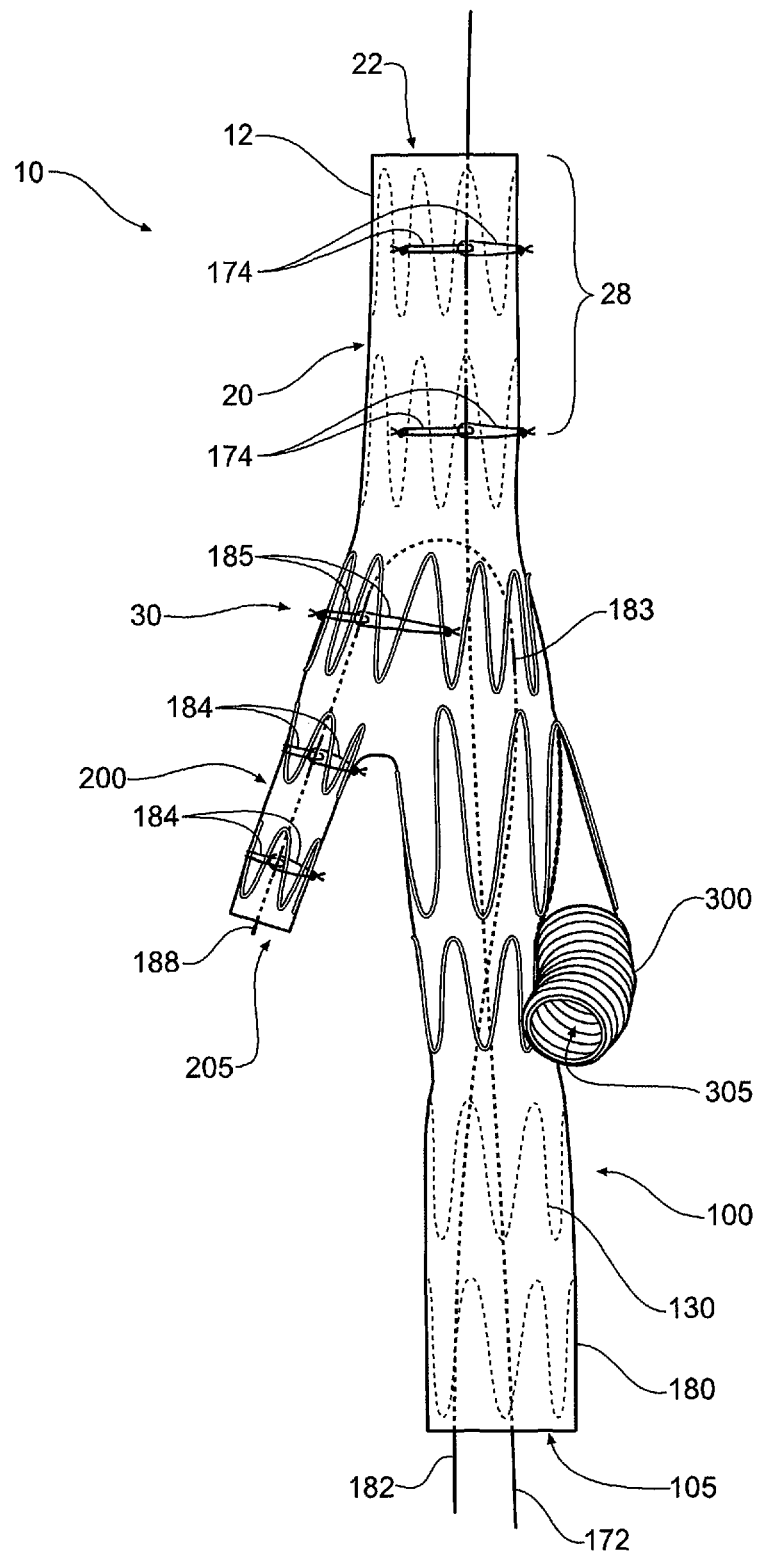
FIG. 1b shows the stent graft of FIG. 1a reduced with the use of diameter reducing ties.
Figure 1D:
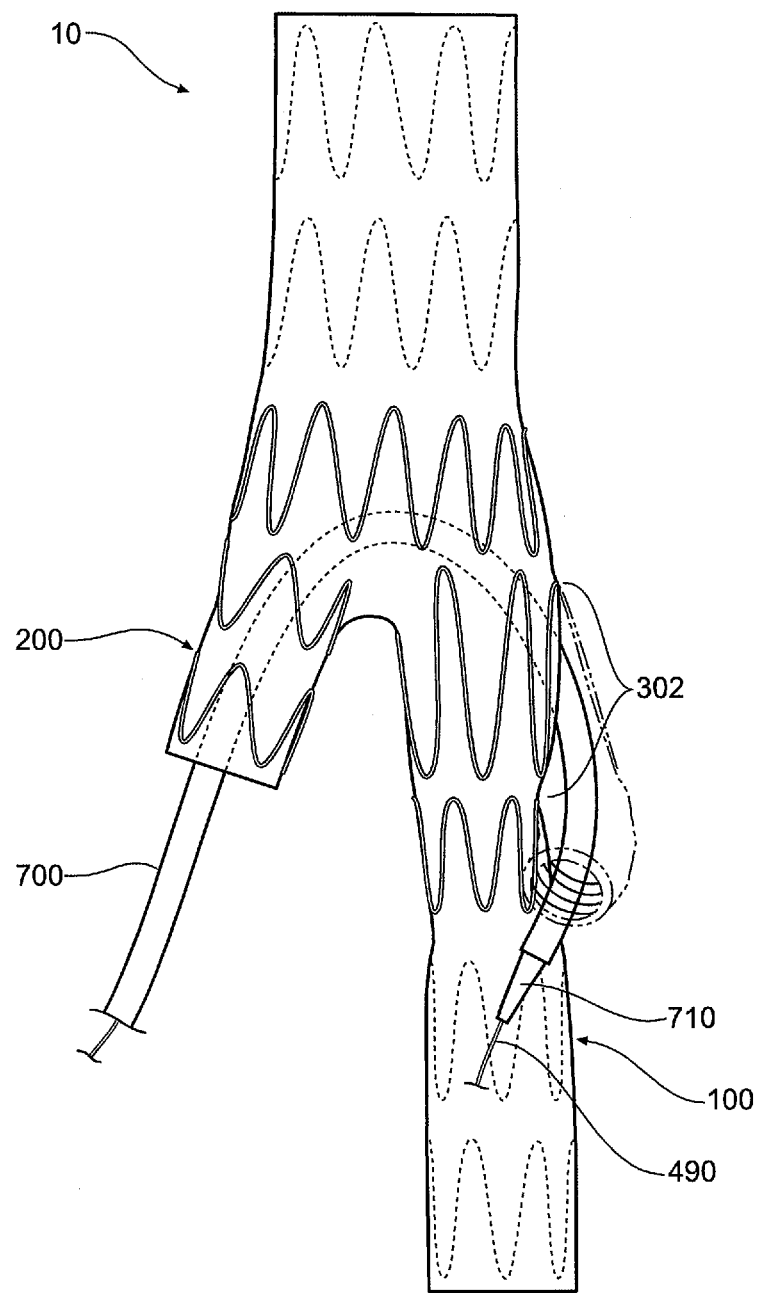
FIG. 1d is similar to FIG. 1c, but shows the lateral opening into the side arm more clearly by omitting the side arm.

Referring now FIGS. 1c and 1d, it can be seen that the side arm lumen 305 is in fluid communication with the first leg lumen 105 at the bifurcation 17. The cross-sectional views of FIGS. 1e, and 1f, taken through sections lines e-e and f-f respectively (shown on FIG. 1c), show the combined and expanded lumen 27 at the bifurcation. The combined lumen 27 extends between the main lumen 22 and a distal portion 108 of the first leg lumen which is shown on FIG. 1g. The combined lumen 27 is bounded laterally by a portion 303 of the side arm 305 as shown in FIGS. 1c, 1e and 1f. It can be seen the amount of lateral room for a delivery device 700 in an "up and over" procedure is enhanced by the increased widths $W_e$, and $W_f$, shown in FIGS. 1e and 1f. FIG. 1g shows the width $W_G$ available to the delivery device once it has reached down further into the side arm 300.

Referring again to FIGS. 1a, 1b and 1c, it can be seen that the main lumen 22 of the stent graft 10 comprises a divergent portion 30 adjacent to the bifurcation 17. The divergent portion 30 diverges distally. In contrast, normally vessels and stent grafts converge in the direction of the blood flow.

Thus, it can be seen that the stent graft 10 of FIG. 1a is a double bifurcated endovascular graft (for the aortic and iliac bifurcations) which diverges to expand the diameter of the lumen in the region of the iliac aneurysm 501' (most clearly shown in FIG. 4j). It also has a leg 200 which angles towards the contralateral side. By expanding the lumen at the bifurcation, the stent graft 10 ensures that all available space in the aneurysm 501' can be used to increase the up-and-over diameter that a covered stent 720 and its delivery device 700 shown in FIGS. 4i and 4j must negotiate during deployment. It also separates the ipsilateral and contralateral legs 100, 200 so that the aortic bifurcation might extend all the way to the bifurcation of the graft 10 and further increase the up-and-over angle available. The resultant structure of the stent graft 10, as shown most clearly in FIG. 1d and the cross sectional view of FIG. 1f, includes a significantly elongated lateral opening 302 from within the prosthetic trunk into the prosthetic side arm 300. This facilitates cannulation as well as increasing the up-and-over angle available.

With the embodiment of the invention shown in FIG. 1a, the first leg 100 comprises a long leg and the second leg 200 comprises a short leg. It can also be seen that the stent graft comprises a plurality of longitudinally spaced apart self-expanding stents 24, 25, 32, 110, 120, 130, 140, 210 and 220. These self-expanding stents may be made from a super elastic material such as Nitinol. Typically the self-expanding stents comprise zigzag stents, each zigzag stent comprising a plurality of struts and bends, the bends being between adjacent struts. For example, stent 130 shown in FIG. 1a comprises struts 132 and bends 136.

Referring now to FIG. 1b, a stent graft 10 is shown in combination with a pair of temporary diameter reduction constraint arrangements. The first temporary constraint arrangement is a body constraint arrangement comprising a body release wire 172 and a plurality of loops of thread 174, each loop 174 engaged with the body release wire 172 and engaged around a proximal portion of the tube body 20 circumferentially spaced a selected distance away from the body release wire 172, and drawn tight and tied to itself to reduce the proximal portion 28 of the main body 20.

A second temporary diameter reduction constraint arrangement in the form of a leg temporary diameter reduction constraint arrangement is also shown in FIG. 1b. The leg constraint arrangement comprises a leg release wire 182 and a plurality of loops of thread 184, each loop 184 engaged with the leg release wire 182 and engaged around a distal portion 255 of the second leg at a location circumferentially spaced a selected distance away from the leg release wire 182 and drawn tight and tied to itself. This reduces the distal portion 255 of the second leg 200.

The leg release wire 182 is slidably attached to the biocompatible graft material of the stent graft 10 at two spaced apart positions 183 and 185 as is shown in FIG. 1b. The spaced apart positions are in, or adjacent to, the divergent portion 30. The two spaced apart positions 183 and 185 are sufficiently spaced so as to allow the leg release wire 182 to be retracted without excessive force. The expanded lumen at the bifurcation assists in allowing the leg release wire 182 to curve with a larger radius than might otherwise be the case. The spaced apart positions 183 and 185 shown in FIG. 1b may in fact be further spaced apart. The positions shown in FIG. 1b are illustrated for clarity rather than precision.

The leg release wire 182 curves over the bifurcation and exits out through the second leg 200 terminating in a soft tip 188.

The stent graft 10 has an internal self-expanding sealing stent 24 and an outer sealing surface 80 at the proximal end 12 of the main body 20 as shown in FIG. 1a. It also has an internal self-expanding stent 140 and an external sealing surface 180 at the distal end 160 of the first leg 100.

Figure 2:
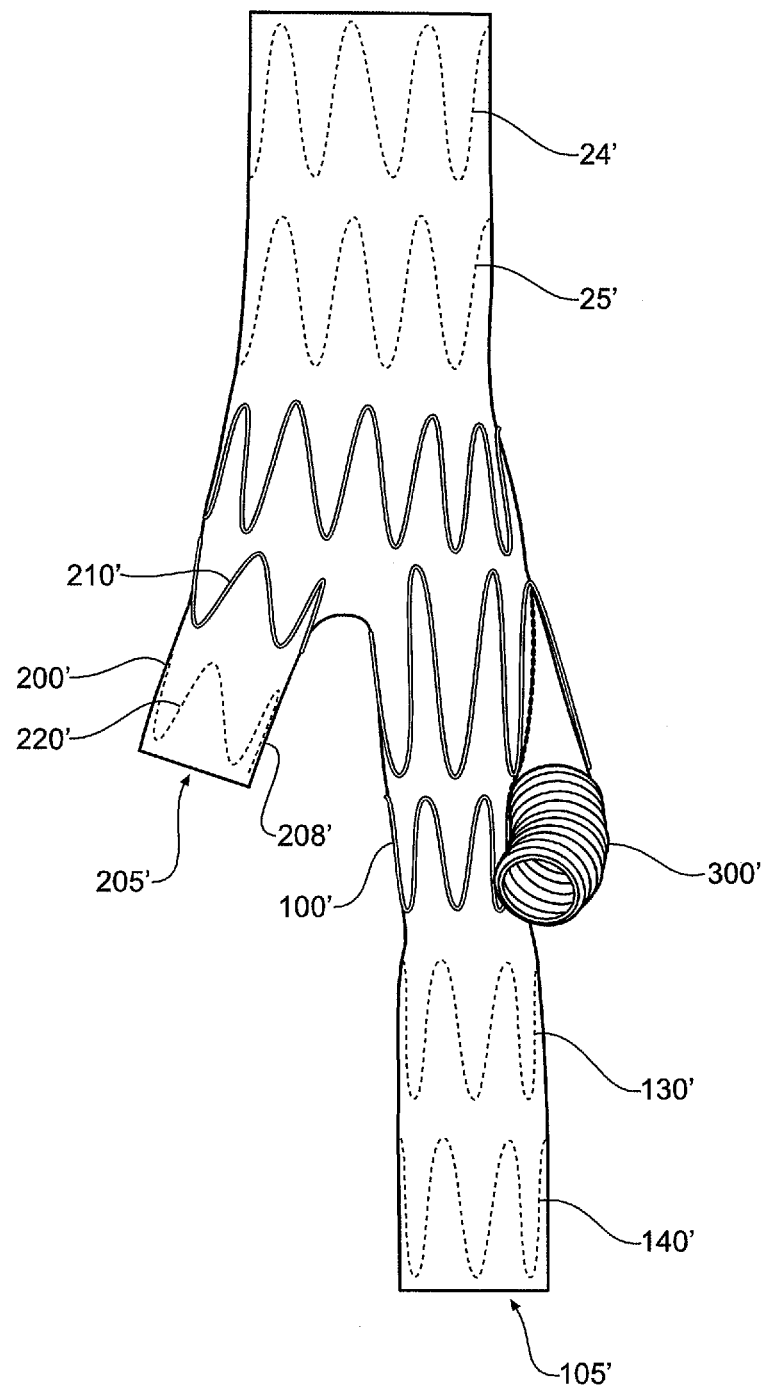
FIG. 2 shows an alternative embodiment of the invention shown in FIGS. 1a, 1b and 1c.

An alternative embodiment of the invention is shown in FIG. 2. With this embodiment of the invention, a stent graft 10' has a second leg 200' with an internal stent 220'. This provides a sealing surface 208' on the short leg 200' of the stent graft 10'.

Turning now to FIG. 1c, it can be seen how the stent graft 10 of the present invention facilitates cannulation of the internal iliac artery. In FIG. 1c a delivery device 700 having a tip 710 tracking over a guide wire 490 is shown.

Figure 3:
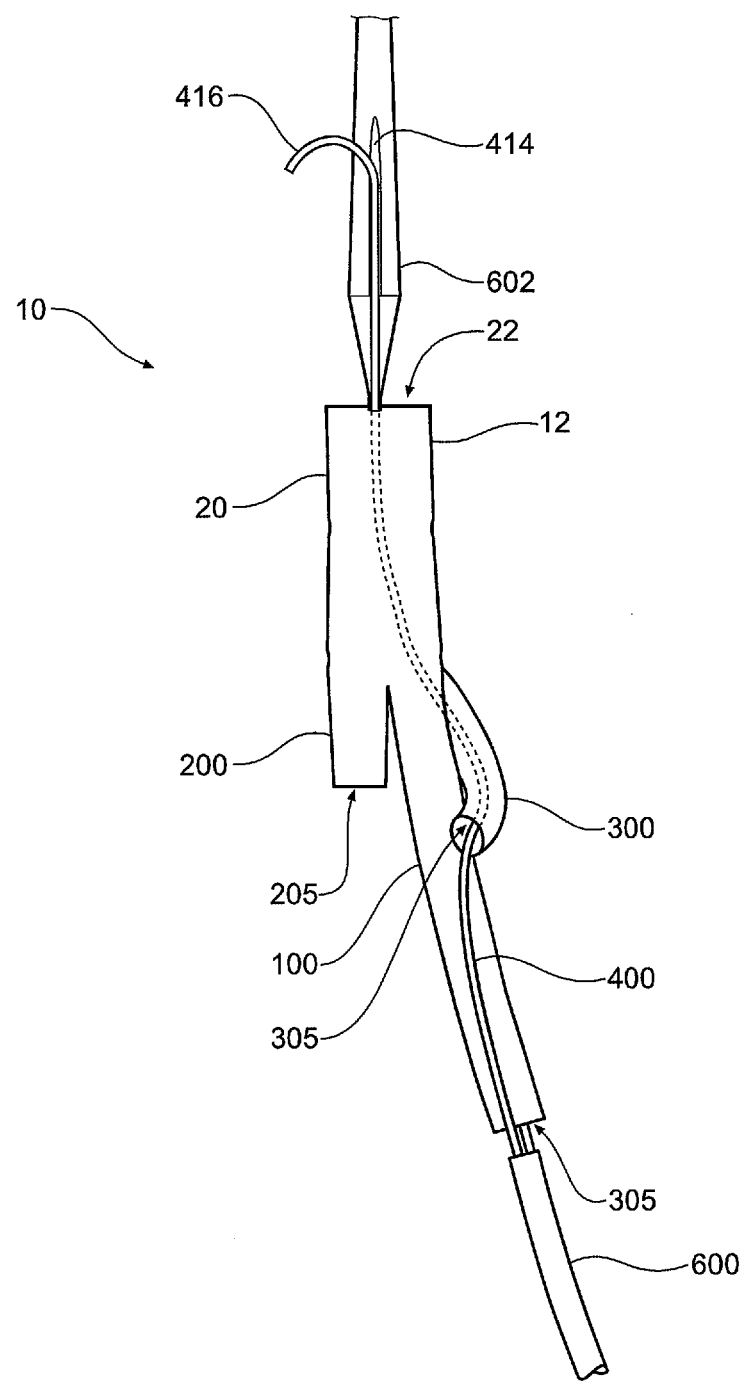
FIG. 3 shows the stent graft of FIG. 1a loaded onto a delivery device in accordance with a further aspect of the invention.

FIG. 3 shows an assembly comprising delivery device 600, a stent graft 10 loaded longitudinally to the delivery device 600 and an indwelling catheter 400. The indwelling catheter 400 passes in through a side arm lumen 300 of the stent graft 10 and extends out through the proximal end 12 of the main body 20 of the stent graft 10.

The delivery device 600 includes a nose cone dilator 602 that has a groove 414. The groove 414 receives a tip 416 on the end of the indwelling catheter 400. The tip 416 is curved to facilitate cannulation of the second leg 200 of the stent graft 10.

Deployment of the stent graft 10 into the vascular system of a patient will now be described.

FIGS. 3 and 4a to 4j show the various stages of deployment of a stent graft according to the embodiment of the present invention shown in FIGS. 4a to 4c.

FIG. 3 shows a schematic version of an embodiment of a stent graft 10 according to the present invention loaded onto a delivery device. For convenience, the sheath of the delivery device has been withdrawn to show the assembly inside it. The delivery device 600 has a nose cone dilator 602 at its proximal end and a stent graft assembly 10 of the invention is mounted onto the delivery device 600. This embodiment of stent graft 10 has a helical side arm 300 on the longer leg 100 of the stent graft.

An indwelling catheter 400 extends from the delivery device 600 through the helical side arm 300 up through the main lumen to a groove 414 in the nose cone dilator 602 outside of the stent graft 10. The indwelling catheter 400 has a flexible curved proximal end 416.

FIG. 4a shows a schematic vasculature of a patient including an aorta 500 renal arteries 504 and an aortic bifurcation 508. Extending from the aortic bifurcation 508 are (common) iliac arteries 510 and 520. The aorta has an aneurysm 501, 501' which extends down the common iliac artery to the position of the internal iliac artery 540. The iliac bifurcation defines the bifurcation between the internal iliac artery 540 and the external iliac artery 560.

FIG. 4a shows a proximal most stent graft 8 deployed into the descending aorta with uncovered suprarenal stents 90 extending over the renal arteries 504 to provide secure fixation.

FIG. 4b then shows a stent graft 10 according to an embodiment of the invention with its proximal end 12 partially inside the stent graft 8 and its shorter second leg 200 released from the delivery device 600, but the longer leg 100 still partially captive within the delivery device 600.

With the stent graft 10 partially deployed as shown in FIG. 4b, it can be maneuvered distally to the position shown in FIG. 4c such that the shorter leg 200 enters the contralateral iliac artery 520 and the crotch 11 (most clearly shown in FIG. 4b) of the stent graft 10 seats against the aortic bifurcation region 509. This is facilitated by the constriction of the leg 200 by diameter reducing ties 184 shown in FIG. 1b.

Once the stent graft 10 is in the position shown in FIG. 4c, the diameter reducing ties 184 are released by retracting their release wire 182. The proximal end 12 of the stent graft 10 is also released from the delivery device 600 when the diameter reducing ties 174 are released by retracting their release wire 172 such that the proximal portion 28 of the stent graft 10 seals into the stent graft 8.

FIGS. 4c to 4e show the indwelling catheter 400 and its flexible curved proximal end 416 directed down into the contralateral iliac artery 520. The flexible curved proximal end 416 facilitates snaring from the contralateral iliac artery 520 with a snare 800 as is shown in FIG. 4d and as is taught in U.S. patent application Ser. No. 11/788,285 entitled "Twin Bifurcated Stent Graft" (US Publication 2007/0250154).

As shown progressively from FIGS. 4f and 4g, the distal end of the long leg 100 is released into the external iliac artery 560 thereby sealing the long leg 100 against the wall of the external iliac artery 560.

Also shown in FIGS. 4f and 4g, is the dilator and sheath introducer 700 having a sheath 750 being advanced over the guide wire 490 in the contra-lateral iliac artery 520 and tracked over the guide wire 490 so that the nose cone 760 of the sheath introducer enters into the side arm 300 until it exits the distal end of the side arm as shown in FIG. 4g.

The sheath introducer nose cone 760 is then withdrawn leaving the sheath 750 in place. At this stage, the indwelling guide wire 490 is still in a through-and-through position. As shown in FIG. 4h, another guide wire 496 is introduced through the sheath 750 and extended from the sheath 750 to enter into the internal iliac artery 540.

As shown in FIGS. 4i and 4j, a side arm deployment device is deployed over the guide wire 496 into the internal iliac artery 540 so that balloon expandable covered stent 720 extends into the internal iliac artery 540 from the side arm 300. The indwelling guide wire 490 is then removed.

A leg extension 290 may then be placed into the short leg 200 of the graft 10 as is shown in FIG. 4j.

Figure 5:
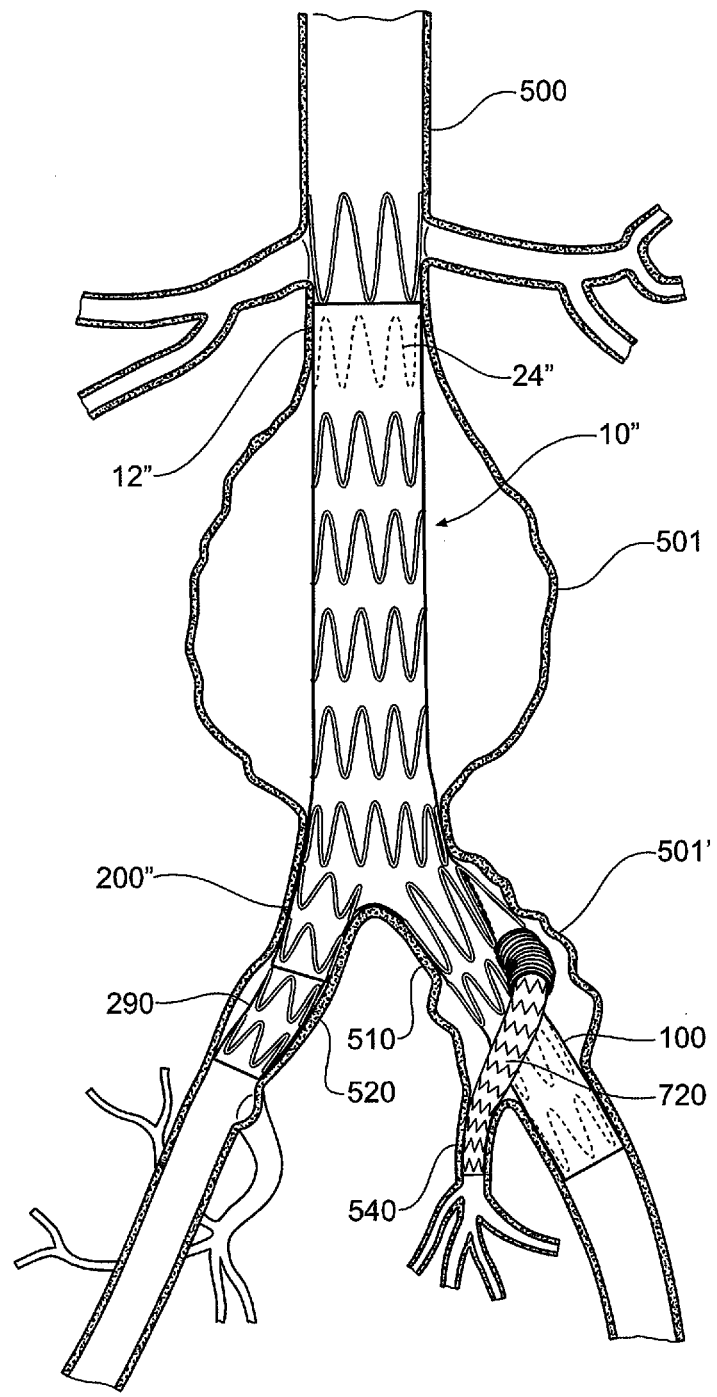
FIG. 5 shows a further embodiment of the invention deployed into the vascular system of the patient.

In other embodiments of the invention, the stent graft 8 and the stent graft 10 can be combined to create a single stent graft 10" as is shown in FIG. 5. This stent graft may be elongated to suit particular anatomies.

With the embodiments of the invention described above, the reverse taper within the stent graft at the region around the bifurcation takes advantage of the expansion in the anatomy due to the aneurysm 501' within the iliac artery to maximise the room available for cannulation of the side arm 300 and then cannulation of the internal iliac artery 540.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft comprising a biocompatible graft material and a plurality of stents, the stent graft comprising:
   a main body comprising a main lumen and having a proximal end and a distal end terminating in a bifurcation;
   first and second legs extending from the bifurcation, the first and second legs having respective first and second leg lumens and the first and second leg lumens being in fluid communication with the main lumen;
   a side arm extending from the first leg, the side arm having a side arm lumen, the side arm lumen being in fluid communication with the first leg lumen at a position laterally adjacent to the bifurcation; and
   a combined lumen, the combined lumen extending laterally from the main lumen and bounded laterally by a portion of the side arm located longitudinally at the point where the bifurcation begin from the proximal to the distal direction.

2. The stent graft as claimed in claim 1, wherein the main lumen comprises a divergent portion adjacent to the bifurcation, the divergent portion diverging distally.

3. The stent graft as claimed in claim 2, wherein the combined lumen diverges distally.

4. The stent graft as claimed in claim 3, wherein the first leg comprises a long leg and the second leg comprises a short leg, the long leg longer than the short leg.

5. The stent graft as claimed in claim 4, comprising a plurality of longitudinally spaced apart self-expanding stents fastened thereto.

6. The stent graft as claimed in claim 5, wherein at least some of the plurality of self-expanding stents comprise zig-zag stents, each zig-zag stent comprising a plurality of struts and bends, the bends being between adjacent struts.

7. The stent graft as claimed in claim 5, comprising a body temporary diameter reduction constraint arrangement, the body arrangement comprising:
   a body release wire; and
   a plurality of loops of thread, each loop engaged with the body release wire and engaged around a proximal portion of the main body circumferentially spaced a selected distance away from the body release wire, and drawn tight and tied to itself to reduce the proximal portion of the main body.

8. The stent graft as claimed in claim 5, comprising a leg temporary diameter reduction constraint arrangement, the leg constraint arrangement comprising:
   a leg release wire; and
   a plurality of loops of thread, each loop engaged with the leg release wire and engaged around a distal portion of the second leg at a location circumferentially spaced a selected distance away from the leg release wire, and drawn tight and tied to itself to reduce the distal portion of the second leg.

9. The stent graft as claimed in claim 8, wherein the leg release wire is slidably attached to the biocompatible graft material at two spaced-apart positions in, or adjacent to, the divergent portion,
   whereby the two spaced-apart positions are sufficiently spaced so as to allow the leg release wire to be retracted without excessive force.

10. The stent graft as claimed in claim 9, wherein the leg release wire curves over the bifurcation and exits out through the second leg.

11. The stent graft as claimed in claim 9, wherein the zig-zag stent comprises super elastic material.

12. The stent graft as claimed in claim 10, wherein the side arm extends part helically around the first leg.

13. The stent graft as claimed in claim 12, wherein the side arm comprises a self-expanding helical coil stent.

14. The stent graft as claimed in claim 13, wherein the proximal end of the main body comprises an internal self-expanding sealing stent and an outer sealing surface.

15. The stent graft as claimed in claim 14, wherein the distal end of the first leg comprises an internal self-expanding stent and an external sealing surface.

16. An assembly comprising:
   a delivery device;
   the stent graft as claimed in claim 1 loaded onto the delivery device; and an indwelling catheter passing in through the side arm lumen of the side arm and out through the proximal end of the main body.

17. The assembly of claim 16, comprising a nose cone dilator, the nose cone dilator comprising a groove, the groove receiving a tip on an end of the indwelling catheter.

18. The assembly of claim 17 wherein the tip is curved to facilitate cannulation of the second leg.

\* \* \* \* \*